(12) United States Patent
Zagury et al.

(10) Patent No.: US 7,022,326 B1
(45) Date of Patent: *Apr. 4, 2006

(54) CARBOXYMETHYLATED RETROVIRAL REGULATORY PROTEINS AND INTERFERON-α

(75) Inventors: Jean-François Zagury, Paris (FR); Jay Rappaport, Balacynwyd, PA (US); Miguel Carcagno, Buenos Aires (AR)

(73) Assignees: Biovacs, Inc., Wilmington, DE (US); Neovacs (FR)

(*) Notice: Subject to any disclaimer, the term of this patent is extended or adjusted under 35 U.S.C. 154(b) by 0 days.

This patent is subject to a terminal disclaimer.

(21) Appl. No.: 09/572,451

(22) Filed: May 17, 2000

(Under 37 CFR 1.47)

Related U.S. Application Data (63) Continuation of application No. PCT/US98/27263, filed on Dec. 22, 1998.

(30) Foreign Application Priority Data

Dec. 26, 1997 (FR) ............................................ 97 16589

(51) Int. Cl.
*A61K 39/00* (2006.01)

(52) U.S. Cl. ................................ 424/192.1; 424/188.1; 424/208.1; 530/350; 530/333; 530/344; 530/345; 530/826

(58) Field of Classification Search ................. 530/350, 530/333, 344, 345, 826; 424/188.1, 192.1, 424/208.1
See application file for complete search history.

(56) References Cited

U.S. PATENT DOCUMENTS

| 6,132,721 A | * | 10/2000 | Zagury et al. | ............ | 424/187.1 |
| 6,200,575 B1 | * | 3/2001 | Zagury et al. | ............ | 424/208.1 |
| 6,420,141 B1 | | 7/2002 | Zagury et al. | | |

FOREIGN PATENT DOCUMENTS

| WO | WO 86/06414 | 11/1986 |
| WO | WO 91/18454 | 11/1991 |
| WO | WO 94/15634 | 7/1994 |
| WO | WO 95/31999 | 11/1995 |
| WO | WO 96/27389 | 9/1996 |
| WO | WO 99/33872 | 7/1999 |

OTHER PUBLICATIONS

Kirsch, T., et al., "Cloning, High–Yield Expression in *Escherichia coli* and Purification of Biologically Active HIV–1Tat Protein," *Protein Expression and Purification* 8:75–84, Academic Press, Inc (1996).

Protzman, W.P., et al., "Immunoradiometric Assay of a Recombinant Human Alpha–2 Interferon (SCH 30500)," *J. Clin. Microbiol.* 22:596–599, American Society for Microbiology (1985).

Aldridge, D.R. et al., "Binding of Nef to Cellular Kinases In Vitro Is Redox–Dependent," *Annu. Conf. Australasian Soc. HIV Med.* 9:125–125, Poster No. P22 (1997).

Azad, A.A. et al., "Large–scale production and characterization of recombinant human immunodeficiency virus type 1 Nef," *J. Gen. Virol.* 75:651–655 (1994).

Frankel, A.D. and C.O. Pabo, "Cellular Uptake of the Tat Protein from Human Immunodeficiency Virus," *Cell* 55:1189–1193 (1988).

Goeddel, D.V. et al., "The structure of eight distinct cloned human leukocyte interferon cDNAs," *Nature* 290:20–26 (1981).

Gringeri, A. et al., "A Randomized, Placebo–Controlled, Blind Anti–AIDS Clinical Trial: Safety and Immunogenecity of a Specific Anti–IFNα Immunization," *J. Acquired Immune Deficiency Syndromes* 7:978–988 (1994).

Gringeri, A. et al., "Absence of Clinical, Virological, and Immunological Signs of Progression in HIV–1–Infected Patients Receiving Active Anti–Interferon–α Immunization: A 30–Month Follow–Up Report," *J. Acquired Immune Deficiency Syndromes and Human Retroviral.* 13:55–67 (1996).

Norley, S. and R. Kurth, "Vaccination against HIV," *Immunobiol.* 184:193–207 (1992).

Moy, P. et al., "Tat–Mediated Protein Delivery Can Facilitate MHC Class I Presentation of Antigens," *Molecular Biotechnol.* 6:105–113 (1996).

(Continued)

*Primary Examiner*—Jeffrey Stucker
(74) *Attorney, Agent, or Firm*—Sterne, Kessler, Goldstein & Fox P.L.L.C.

(57) ABSTRACT

This invention relates to retroviral regulatory proteins or fragments thereof, or interferon alpha protein or fragments thereof, which are carboxymethylated. This chemical modification leads to new proteins or fragments which are biologically inactive but preserve their immunogenicity (toxoids). These proteins or fragments thereof, or interferon alpha or fragments thereof, can be utilized in the treatment and prevention of retroviral infections. The invention also relates to a pharmaceutical composition comprising at least one carboxymethylated protein or fragment of the invention, together with a pharmaceutically acceptable carrier. The invention also relates to a vaccine comprising at least one of the carboxymethylated proteins or fragments of the invention, together with an immunologically acceptable carrier. The invention also relates to a process for obtaining an immunogenic yet not toxic retroviral regulatory protein or fragment, or interferon alpha or fragment. The invention also relates to a method of inducing an immune response in a mammal, comprising administering the vaccine of the invention to a mammal in an immunologically effective amount.

10 Claims, 1 Drawing Sheet

OTHER PUBLICATIONS

Quan, N. et al., "In vivo Induction of Interleukin–1 Bioactvity in Brain Tissue after Intracerebral Infusion of Native gp120 and gp160," *Neuroimmunomodulation* 3:56–61 (1996).

Spanjaard, R.A. et al., "The cysteines in position 1 and 86 of rat interferon$\beta_1$ are indispensable for antiviral activity," *FEBS Letters* 249:186–188 (1989).

Weissmann, C. and H. Weber, "The Interferon Gens," *Prog. Nucl. Acids Res. & Molec. Biol.* 33:251–301 (1986).

Zagury, J.–F. et al., "A critical role of Tat and IFN$\alpha$ in the HIV–1–induced immunosuppression leading to AIDS," *Cellular Pharmacol.* 3:97–103 (1996).

Zagury, D. et al., "Interferon $\beta$ and Tat involvement in the immunosuppression of uninfected T cells and C–C chemokine decline in AIDS," *Proc. Natl. Acad. Sci. USA* 95:3851–3856 (1998).

Zoon, K.C., "Human Interferons: Structure and Function," *Interferon 9*, Ion Gresser, ed., Academic Press Inc. Ltd., London, England, pp. 1–12 (1987).

Rappaport, J., et al., "HIV–1 TAT Toxoid: Rationale for a TAT Vaccine and Results of a Phase I Clinical Trial," *J. Neurol.* 4:364 (1998).

Supplementary European Search Report for EP 98 96 4219, (Aug. 2000).

* cited by examiner

FIG. 1

CARBOXYMETHYLATED RETROVIRAL REGULATORY PROTEINS AND INTERFERON-α

This application is a continuation of PCT/US98/27263, filed Dec. 22, 1998.

FIELD OF THE INVENTION

This invention relates to retroviral regulatory proteins or fragments thereof, or interferon alpha protein or fragments thereof, which are carboxymethylated for use in the treatment and prevention of retroviral infections.

BACKGROUND OF THE INVENTION

AIDS is induced by the HIV-1 virus. HIV- 1 not only directly kills infected CD4(+) T cells, but also induces immunosuppression of uninfected T cells. Two immunosuppressive proteins, interferon alpha and extracellular Tat, mediate this process.

It is known that interferons exert a broad spectrum of biological activity such as anti-viral, anti-proliferative and immunomodulatory activities. As appreciated by those skilled in the art, interferon is a low-molecular weight polypeptide produced as an excretion from various types of mammalian cells. Its properties, chemical nature and methods of preparation have been extensively studied and documented. Currently, three major types of human interferons are known, each differentiated according to the initial producer cell and the inducer applied. They are interferons alpha (leukocyte), beta (fibroblast) and gamma (immune).

Interferon alpha was among the first of the cytokines to be produced by recombinant DNA technology and has been shown to have therapeutic value in conditions such as inflammatory, viral, and malignant diseases.

The HIV-1 virus is composed of several proteins. Among these proteins, the Tat and Nef proteins are the earliest produced within the viral cycle. As previously mentioned, extracellular Tat protein has immunosuppressive activity. The Tat protein is also an efficient activator of HIV gene expression.

Several approaches have been proposed to fight against the effects of Tat protein, such as genetic approaches to block the transcriptional action of Tat. Clinical trials have been performed with antisense RNA (Hybridon, Inc.), and in vitro experiments have shown the feasibility of ribozymes that use RNA of the TAR region (Tat binding site in RNA) to block the transcriptional action of Tat. Some pharmacological molecules inhibiting the transcriptional effect of Tat have also been described. All these methods were intended to block virus replication by blocking Tat-transcriptional activity.

Immunological methods have also been proposed. WO-A-91/18454 reports the utilization of retroviral protein polypeptides, including the native Tat protein, obtained by proteolytic degradation, chemical synthesis or genetic recombination, for specific immunizations. These retroviral protein polypeptides are used as immunogens to prevent retroviral replication and cytotoxic activity, particularly against the lymphocytes and neural cells affected by retroviral proteins like Tat. However, the toxicity of native proteins or their fragments precludes their utilization for immunization.

WO-A-95/31999 reports the utilization of the HIV-1 native Tat protein, fragments of the protein or polypeptides with deletions/substitutions, as immunogens to block HIV-1 replication by blocking the uptake of extracellular Tat protein by non-infected cells. In spite of the described immunogenicity of the compounds reported in WO-A-95/31999, certain concerns remain such as the toxic effects of native Tat protein, the immunological disorders induced by it, and the absence of neutralizing antibodies by immunization with the described immunogens. Therefore, there is a need for developing new Tat inactivated immunogens which have lost all the harmful effects of native Tat protein and which are also capable of inducing cellular and/or humoral immunological responses.

WO-A-96/27389 reports the utilization of Tat toxoids and retroviral regulatory proteins as immunogens capable of inducing an immunological response against the native Tat protein and preventing or repairing its immunosuppressive effects. These toxoids, inactive but immunogenic products, have been prepared by chemical treatment with formaldehyde of the native protein or segments derived from this protein. However, aldehyde inactivation is not readily reproducible. For industrial production, regular results are needed, especially regarding inactivation procedures. Constant structure and well-defined products are also preferred. An ideal product should also have a good stability period.

SUMMARY OF THE INVENTION

Accordingly, the present invention has the aim of providing new carboxymethylated toxoids and a new simple and efficient method of producing these toxoids for anti-retroviral use. These toxoids are derived mainly from HIV-1 regulatory proteins or from interferon alpha, both of which contribute to the immunosuppressive effect in HIV-1 infections. Among these regulatory proteins, Tat, Nef, Vpr, and Vif are primarily discussed.

The toxoid strategy has large advantages with respect to an amino acid substitution/deletion strategy. The native Tat protein regions responsible for pleomorphic Tat effects are not well-defined, and it is difficult to predict the substitutions/deletions to ensure the total innocuity of a preparation.

For example, a C-G mutation at amino acid position 25 of the Tat protein destroys the transactivator effect of Tat without eliminating its immunosuppressive effect. Furthermore, amino acid substitutions/deletions can strongly alter the structure of the modified molecule with respect to the native molecule (linear and conformational antigens), and thus preclude the development of an appropriate immunological reaction against the native molecule. This last point is particularly important because of the need to generate neutralizing antibodies against the native protein.

The present invention thus relates to a retroviral regulatory protein or fragment thereof, or to interferon alpha or fragment thereof, which is carboxymethylated.

In a preferred embodiment, the protein or fragment thereof is derived from HIV-1, HIV-2, HTLV-1 or HTLV-2, and preferably from HIV-1 or HIV-2. The protein or fragment thereof is a protein or fragment of retroviral regulation activity. HIV-1 viral regulatory proteins are mainly Tat, Nef, Vpr and Vif.

In another embodiment of the invention, the protein or fragment thereof derives from the Tat protein, preferably from the Tat protein of HIV-1.

In another aspect of the present invention, the carboxymethylated retroviral regulatory protein or fragment thereof, or the carboxymethylated interferon alpha or fragment thereof, is used in therapeutic treatment. The medicines derived from the present invention find their utility, for example, in the curative or preventive treatment of retroviral infections generally, or specifically from the deleterious effects caused by interferon alpha overproduction or from the effects caused by a regulatory protein from a virus, preferably HIV-1.

In yet another aspect of the invention there is provided a pharmaceutical or vaccine composition comprising the immunogenic compounds of the present invention. The immunogenic compound can be administered alone, together with another immunogenic compound of the present invention, and/or together with an acceptable pharmaceutical carrier such as an adjuvant or with other retroviral immunogens.

The present invention also relates to a process for the preparation of an immunogenic yet not toxic retroviral regulatory protein or fragment thereof, or interferon alpha or fragment thereof, characterized by the fact that the regulatory viral protein or fragment thereof, or the interferon alpha or fragment thereof, is carboxymethylated, and the compound is then isolated, if desired.

In another embodiment of the invention, in performing the process described above, the protein or fragment thereof is fused to a compound which permits its purification. For example, the protein or fragment thereof is fused to a peptide fragment containing several histidines, preferably 4.5 or 6, or even more histidines in tandem, which permits fixation to Nickel-bound resins of an affinity column for a purification step. In a preferred embodiment, this peptide is cleaved after purification.

In another embodiment of the invention, the regulatory retroviral protein or fragment thereof, or interferon alpha or fragment thereof, can be prepared by recombinant DNA technology or biochemical synthesis and purification. After using recombinant DNA methods, the produced protein or fragment thereof, or interferon alpha or fragment thereof, can be purified by affinity chromatography using, for example, antibodies raised against the regulatory protein or interferon alpha or one of their fragments. A fusion protein containing the protein or fragment thereof fused to a fusion peptide, which functions as linker for an affinity column, can also be synthesized.

In another embodiment of the invention there is provided a method of inducing an immune response in a mammal, including both humoral and/or cellular, the method comprising administering a pharmaceutical or vaccine composition with at least one carboxymethylated retroviral regulatory protein, or interferon alpha or fragment thereof, together with an acceptable pharmaceutical carrier, in a sufficient amount to induce an immune response.

In yet another embodiment of the invention there is provided a method of raising antibodies in a mammal, the method comprising administering a pharmaceutical or vaccine composition with at least one carboxymethylated retroviral regulatory protein, or interferon alpha or fragment thereof, together with an acceptable pharmaceutical carrier, in an amount sufficient to raise antibodies in a mammal.

DETAILED DESCRIPTION OF THE INVENTION

Figure 1:
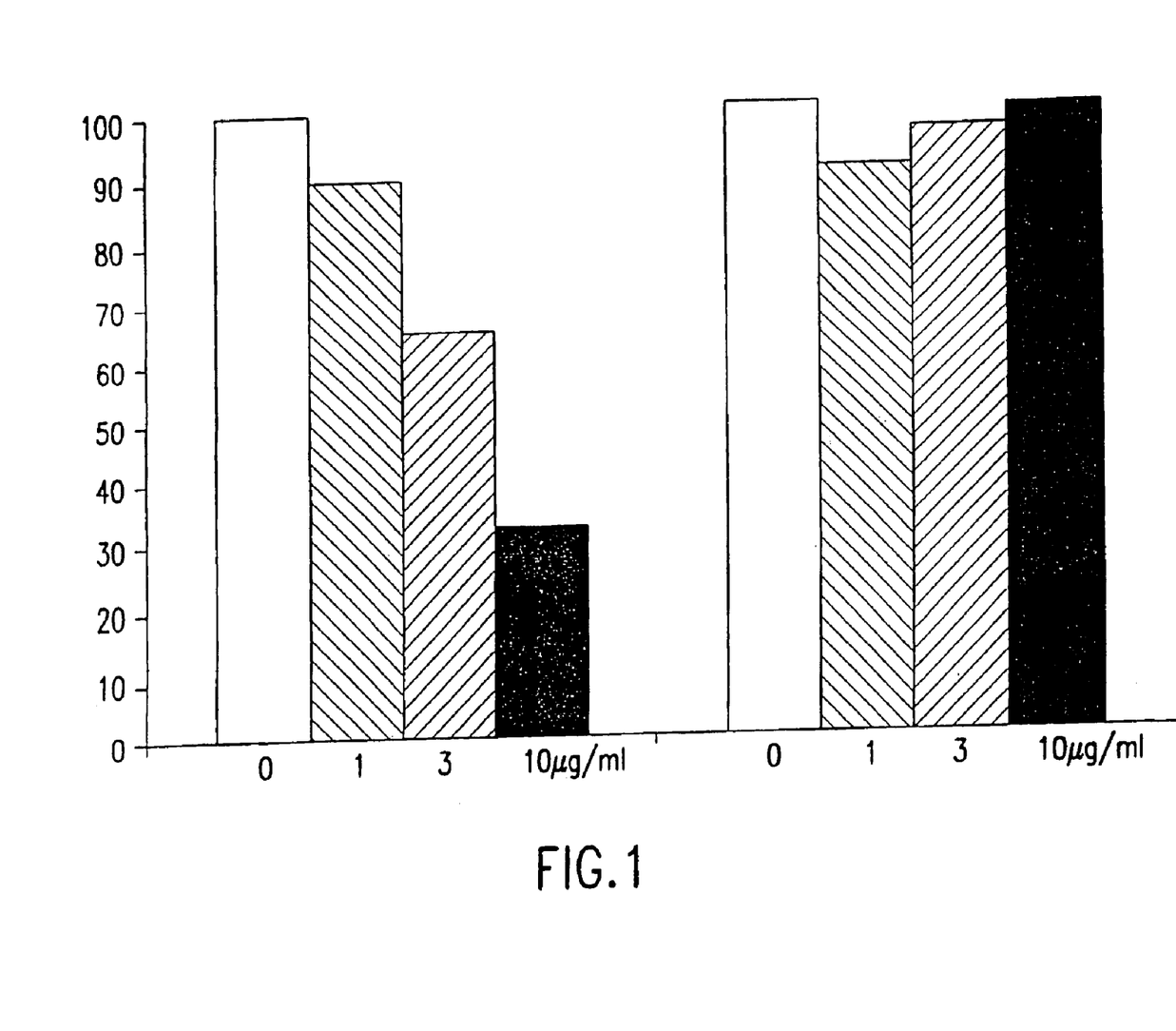
FIG. 1 represents the results of the effects of native Tat compared to those of the product of Example 1 on normal lymphocyte proliferation.

According to this invention, the proteins or fragments which behave like toxins for the immune system, whether overproduced interferon alpha, Tat or Nef, for example, are modified by carboxymethylation. This chemical modification leads to new proteins or fragments which are biologically inactive but preserve their immunogenicity (toxoids). The native proteins or fragments which behave like toxins for the immune system are recognized by the antibodies raised against the presently claimed carboxymethylated proteins or fragments. The carboxymethylated proteins or fragments preserve immunogenic properties sufficient to create neutralizing antibodies or block native protein, and at the same time have lost at least 90% to about 95% or even 99% of biological toxic properties of the native protein or fragment.

A carboxymethylated immunogenic compound according to this invention can comprise the whole regulatory protein or a fragment thereof. Furthermore, it can comprise, as known by one skilled in art, one or more modifications of the amino acids of the protein or fragment, such as deletions, substitutions, additions or functionalization, like acylation of amino acids, as long as these modifications allow the compound to retain the absence of toxicity and active immunological features. For example, a leucine residue replacement by an isoleucine residue does not modify those properties. The modifications should generally involve less than 30% of the amino acids, preferably less than 20%, more preferably less than 10%.

Further guidance concerning which amino acid changes are likely to have a significant deleterious effect on a function can be found in Bowie, J. U., el al., "Deciphering the Message in Protein Sequences: Tolerance to Amino Acid Substitutions," *Science* 247:1306–1310 (1990).

To obtain the fragments of the present invention, the respective proteins can also be digested. These proteins may be digested with enzymes such as an endopeptidase or a protease (e.g., trypsin, chymotrypsin) or with chemical reagents such as cyanogen bromide, as known in the art.

In general, a fragment according to the present invention can be as long as necessary to preserve immunogenicity and avoid toxicity. For example, a peptide fragment of the present invention can have 8 to 110 amino acids, preferably 12 to 60 amino acids, or even 12 to 40 amino acids. Such a fragment can also have one or more, most preferably 1 to 5, supplementary amino acids at the C or N-terminus which are different from the amino acids adjacent to the original segment. A fragment must also have at least one cysteine to be carboxymethylated. In addition, all methods related to modifications, homology or similarity between the modified immunogen and the protein or part of it, as well as the dimensions of the immunogenic compound, and also the ways of utilization, or the coupling of the immunogenic compound according to the present invention can be elucidated by reference to another immunogenic protein such as tetanus toxoid (WO-A-86/06 414 or EP-A-0 220 273 or even PCT/US 86/00831, the disclosure of which is hereby incorporated by reference).

The immunogenic compounds according to the present invention derived from regulatory proteins will be named "viral toxoids" in the experimental section. In fact, as classic bacterial toxoids of the prior art, the compounds of the present invention are deprived of their own toxicity, but nevertheless, they are able to provoke an immune response when administered to an organism.

In order to verify that the native regulatory protein is well-recognized by the antibodies raised against the carboxymethylated regulatory protein or fragment, the native protein can be immunologically assayed, for example, by ELISA methods. The assay is carried out in the presence of specific antibodies raised against carboxymethylated poly or oligopeptides of the invention, and Ag-Ab complex formation is determined, as known in the art and as shown in the experimental section. For example, competitive or sandwich immunoassays can be used.

To determine whether the immunogenic properties of the regulatory protein have been sufficiently conserved/preserved to create neutralizing antibodies for the native protein, mammals (rabbits, rats, mice) can be immunized with the help of an immunogenic carboxymethylated compound according to the invention. Subsequently, it can be verified whether the produced antibodies neutralize the toxic native protein activities, as demonstrated in the experimental section.

In order to determine if the carboxymethylated regulatory protein has lost at least 90% of its toxic biological properties, in the case of Tat, the effect of inactivated Tat on the immunosuppression of T cells or on neoangiogenesis can be studied.

The regulatory protein Tat inactivation is verified, for example, by a Tat rescue assay using a Tat-deficient HIV non-infectious mutant cultured in the HL-1 cell line, where replication depends on the exogenous supply of native Tat.

The immunogenic compound of the present invention can be derived preferably from any regulatory protein of the HIV-1, HIV-2, HTLV-1 or HTLV-2 viruses, more preferably Nef, Rev or Vpr, and most preferably Tat from the HIV-1 or HIV-2 viruses.

The immunogenic compound of the present invention can also be derived from the Tax protein of the HTLV-1 or HTLV-2 viruses.

Interferon alpha is readily available. For example, natural human interferon alpha has been purified from several cell sources including leukocytes isolated from whole blood, neonatal fibroblasts, lymphoblastoid and various leukemic cell lines. For a review of available purification schemes used for recombinant interferon alpha, see T. L. Nagabhushan and P. P. Trotta, Ulrnann's *Encyclopedia of Industrial Chemistry* A14, VCH: 372 (Weinheim, Federal Republic of Germany 1989).

Human interferon alpha is derived from a family of several different genes. More than 24 species have been identified so far from gene and protein sequence data. Most of the species have a signal peptide sequence of 23 amino acid residues and a mature amino acid sequence of 166 amino acid residues (Goeddel, D. V. et al., *Nature* 290:20–26 (1981); Weissmann, C. and Weber, H., *Prog. Nuc. Acid Res. Mol. Biol.* 33:251–300 (1986); Zoon, K. C., *Interferon* 9:1–12 (1987)).

Other starting proteins or fragments for use in the present invention are either known products, described in the literature by Frankel, A. D., et al. (Cellular uptake of the Tat protein from human immnunodeficiency virus, *Cell* 55:1189–1193 (1988)) or for HIV-1 Nef, by Azad, A. A., et al. (Large scale production and characterization of recombinant human immunodeficiency virus type 1 Nef, *J. Gen. Virol.* 75:651–55(1994)) or can be prepared by conventional methods.

Particularly, proteins or fragments described above can be prepared by:
(a) synthesis by recombinant DNA technology or biochemical synthesis; and
(b) purification.

After using recombinant DNA methods, the produced protein or fragment thereof, or interferon alpha or fragment thereof, can be purified by affinity chromatography using, for example, antibodies raised aoainst the protein or interferon alpha or one of their fragments. A fusion protein (FP), comprising the protein of the present invention or fragment thereof and a fusion peptide (e.g., histidine-rich oligopeptide) which aids in a purification step by acting as a linker for an affinity column, can also be synthesized. A fusion protein comprising a carboxymethylated retroviral regulatory protein or fragment thereof, or interferon alpha protein or fragment thereof, is another embodiment of the present invention.

In another embodiment for the above described procedure, in which the protein or fragment thereof is fused to a fusion peptide, the fusion protein may be subjected to:
a concentration step, for example, by ultrafiltration;
a desalting step, for example, by gel filtration;
a cyanogen bromide treatment or enterokinase digestion to cleave the fusion protein and release the protein or fragment;
a concentration and diafiltration step;
a cation exchange chromatography step; and
a concentration by ultrafiltration step, followed by an exclusion gel filtration.

The cyanogen bromide reaction described above permits thioether cleavage. The cyanogen bromide action over polypeptide molecules is selective in performing a cleavage at the level of existing methionine residues. This reaction results in the formation of two polypeptide fragments per methionine residue. This reaction can be advantageously coupled to the carboxymethylation reaction described, but it is not necessary for the inactivation.

The present invention also relates to a process for the preparation of an immunogenic yet not toxic retroviral regulatory protein or fragment thereof, or to interferon alpha or fragment thereof, characterized by the fact that the regulatory viral protein or fragment thereof, or the interferon alpha or fragment thereof, is carboxymethylated, and the compound is then isolated, if desired.

The carboxymethylation reaction permits modification of thiol groups present in the cysteine (sulphydryl groups) of the amino acid chain. These groups react with iodoacetic acid or iodoacetamide in a S-carboxymethylation or S-carboxamide-methylation, respectively. The reaction product in each case is an S-carboxy methylcysteinyl or S-carboxy-methylamidocysteinyl residue. In general, at least one of the thiol groups should be modified by the carboxymethylation reaction. To obtain the compounds of the present invention as many thiol groups should be modified by carboxymethylation as necessary to preserve substantial immunogenicity and avoid substantial toxicity.

In the case of Tat protein, there are 7 cysteine residues. These cysteine residues participate in the inter or intra-chain disulphide bridge formation and contribute to oligomer formation. The human, bovine, murine and rat interferon alpha families contain 4 conserved cysteines that are involved in disulfide bridges (e.g., see Spanjaard, R. A., el al., *FEBS Lett.* 249:186–88 (1989)).

The carboxymethylation reaction can also be performed with other chemical reagents, such as performic acid, 3-bromopropionic acid, ethyleneimine, 2-bromoethyl trimethylammonium bromide, 2-bromoethansulphonate, 1,3-propane sulphone, as well as others known to those of skill in the art (e.g., see Means, G. E. and Feeney, R. E, *Chemical Modification of Proteins*, Holden-Day, Inc., San Francisco, Calif. (1971)).

In another embodiment of the invention, in performing the process for preparation of the immunogenic compounds described above, the protein or fragment thereof is coupled to a compound which permits its purification. For example, the protein or fragment thereof is fused to a peptide fragment containing several histidines, preferably 4, 5 or 6, or even more histidines in tandem, which permits fixation to Nickel-bound resins of an affinity column for a purification step. In a preferred embodiment, this oligopeptide is cleaved after purification.

If the presence of this histidine-rich peptide does not induce any toxicity and/or adversely modifies the protein's (or fragment's) immunogenicity, it is not necessary to cleave it after purification. However, under preferred conditions, this compound is cleaved for its removal.

The compounds of the present invention, as well as their pharmaceutically acceptable salts and acids, have significant pharmacological properties. They are biologically inactive with regard to functions usually exerted, such as the immunosuppressive effects, the HIV-1 promoter transactivator effects, the Tat oxidative effects, the anti-vesicular stomatitis virus (VSV) effects on the MDBK system, or the immunosuppressive effects of interferon alpha.

The compounds of the present invention are immunogenic in mice, as well as in humans. They elicit the induction of a humoral immune response with neutralizing antibodies, as well as a cellular immune response.

Accordingly, this invention also relates to a carboxymethylated protein or fragment thereof, or interferon alpha or fragment thereof, for utilization in a therapeutic treatment involving humans or animals; that is, like a medicine.

Medicines derived from the present invention find their utility, for example, in the curative or preventive treatment from the harmful effects provoked by interferon alpha overproduction, or by the effects of a regulatory protein from a virus, mainly a retrovirus such as HIV-1, HIV-2, HTLV-1 or HTLV-2.

The retroviral regulatory proteins for use in the present invention, such as Tat, Nef, Vpr, and Vif, have relatively well-preserved regions. In certain cases, the same subject could be immununized with toxoids derived from variable strains, mostly for the adaptation to geographic variants of epidemics.

A compound according to the invention can be administered by any conventional route in use in the vaccine domain, such as subcutaneous, intramuscular, intravenous or oral. Administration can be as a single dose or repeated doses one or more times after a certain period.

The immunogenic compounds of the present invention can be used as follows: The inventive immunogenic compound is administered to a patient via subcutaneous or intramuscular route in sufficient amounts for the efficacy of the therapeutic schedule on a subject who requires this type of treatment. The administered dose can range from 50 to 1000 µg by intramuscular route, in emulsion form (o/h) every month, for three months, and then periodically according to the induced serum antibodies (i.e., every 2–6 months).

As a medicine, the proteins or carboxymethylated fragments can thus be incorporated in pharmaceutical compositions designed for intramuscular, intravenous, intradermal and even for oral routes.

The invention also relates to pharmaceutical compounds which involve at least one of the mentioned components as the active ingredient. In these compositions, the active ingredient is advantageously present at physiologically efficient doses; the compositions comprise an effective immunogenic dose of at least one of the active ingredients. The immunogenic compound(s) can be administered alone or mixed with an acceptable pharmaceutical excipient, such as an adjuvant.

These pharmaceutical compositions can be liquid, and be present in pharmaceutical forms currently used in human medicine for vaccines, such as injectable preparations in emulsion form. They are prepared by usual methods known in the art. The active ingredient(s) can be incorporated with usually employed excipients in pharmaceutical compositions such as aqueous vehicles, calcium phosphate, and aluminum, for example.

The vaccine of the present invention may also be employed in such forms as capsules, liquid solutions, suspensions or elixirs for oral administration, or sterile liquid forms such as solutions or suspensions. Any inert carrier is preferably used, such as saline, phosphate-buffered saline, or any such carrier in which the protein fragment or peptide or conjugate vaccine have suitable solubility properties. The vaccines may be in the form of single dose preparations or in multi-dose flasks which can be used for mass vaccination programs. Reference is made to Remington's *Pharmaceutical Sciences*, Mack Publishing Co., Easton, Pa., Osol (ed.) (1980); and *New Trends and Developments in Vaccines*, Voller et al. (eds.), University Park Press, Baltimore, Md. (1978), for methods of preparing and using vaccines.

The vaccines of the present invention may further comprise adjuvants which enhance production of protein-specific antibodies. Such adjuvants include, but are not limited to, various oil formulations such as Freund's complete adjuvant (FCA), stearyl tyrosine (ST, see U.S. Pat. No. 4,258,029), the dipeptide known as MDP, saponin (see U.S. Pat. No. 5,057,540), aluminum hydroxide, and lymphatic cytokine.

Freund's adjuvant is an emulsion of mineral oil and water which is mixed with the immunogenic substance. Although Freund's adjuvant is powerful, it is usually not administered to humans. Instead, the adjuvant alum (aluminum hydroxide) or ST may be used for administration to a human. The protein fragment or peptide vaccine or a conjugate vaccine thereof may be absorbed onto the aluminum hydroxide from which it is slowly released after injection. The vaccine may also be encapsulated within liposomes according to Fullerton, U.S. Pat. No. 4,235,877.

The invention also relates, with respect to pharmaceutical compositions, to:

(a) A pharmaceutical composition comprising as a preventive or curative agent, a viral toxoid or fragment thereof, preferably derived from Tat, according to the invention; or (b) A pharmaceutical composition comprising as a preventive or curative agent, anti-Tat antibodies, F(ab")2 or Fab, produced by immunized organisms against the carboxymethylated protein or its fragment thereof, according to the invention.

The present invention also relates to a process for preparing the above-mentioned pharmaceutical composition characterized by mixing, according to known methods, active ingredients with acceptable excipients which are pharmaceutically acceptable.

Furthermore, the invention relates to a vaccine composition which, in addition to the active ingredient(s) (e.g., Tat, Nef, or interferon alpha toxoids, or mixtures thereof, or derivatives or anti-Tat antibodies), can further comprise another immunogen possessing anti-retroviral properties.

For example, other immunogens include the envelope protein GP 160, the transmembrane protein GP 41 from HIV-1 or their fragments known in the art, the viral capsid gag protein, or even the pol protein.

The invention also relates to a method of inducing an immune response in a mammal, including both humoral and/or cellular responses, the method of which comprises administering a pharmaceutical or vaccine composition with at least one carboxymethylated retroviral regulatory protein, or interferon alpha or fragment thereof, together with an acceptable pharmaceutical carrier, in a sufficient amount to induce an immune response.

The invention also includes a method of raising antibodies in a mammal, the method comprising administering a pharmaceutical or vaccine composition with at least one carboxymethylated retroviral regulatory protein, or interferon alpha or fragment thereof, together with an acceptable pharmaceutical carrier, in an amount sufficient to raise antibodies in a mammal.

Having now generally described the invention, the same will be more readily understood through reference to the following Examples which are provided by way of illustration and are not intended to be limiting of the present invention, unless specified.

Experimental Procedures

Preparation A

*E. coli* bacterial strain N° I- 1964 (deposited at the Collection nationale de cultures de micro-organismes de Paris on Dec. 26, 1997) containing a recombinant plasmid incorporated by transformation, which in turn contains a gene fragment coding for a 6-histidine polypeptide associated with the Tat gene, was cultured as follows:.

Two mL of an inoculum of this strain were incubated in 400 mL of base culture medium (5 g/L yeast extract, 1 g/L tryptone, 1 g/L NaCI) and 40 mL of solution # 1 ($CaCl_2$ $2H_2O$: 0.175 g/L, $MgSO_4$ $7H_2O$: 5.9 g/L, glucose: 6 g/L) at 30° C for 10 h at 250 rpm.

The above-mentioned pre-fermentation step was followed by fermentation, maintaining the dissolved oxygen level under 70% saturation by shaking the control. When the optical density, measured at 650 nm, reached the value of O.D.=6.0, 100 mL of a 3.75% IPTG (isopropyl-β-D-thiogalactoside) sterile solution in deionized water, was added. At the same time, the mediun was supplemented with a sterile 25% yeast extract solution. A solution containing 8.5 g/L $MgSO_4 7H_2O$; 300 g/L glucose, and 106 g/L $(NH_4)_2SO_4$ was also added in order to keep glucose concentration at about or over 2 g/L. The bacterial mass was harvested 4 hr after IPTG addition. A filtration step was performed against a 0.1 M Tris; 0.1 M $NaH_2PO_4$, 1 mM dithiotreitol pH 8.0 buffer solution by counter-current filtration (0.3 μm pore).

Three liters of crude bacterial extract were lysed after 4 passages at a 500 bar pressure through a French press. The lysate was then centrifuged for 15 minutes at 4° C at 5000 rpm. Solid urea was then added to the supernatant fluid to a final concentration of 8 M, and pH is adjusted to 8. Affinity chromatography was then performed on a Ni-agarose column (Qiagen) previously equilibrated with 600 mL buffer A (8 M urea, 0.1 M $NaH_2PO_4$, 0.1 M Tris HCI, 1 mM DTT, pH 8).

After loading, the column was rinsed with 250 mL buffer A, and elution was performed with a discontinuous gradient to obtain the expected fusion protein.

The solution thus obtained was concentrated on Amicon membranes with a molecular weight cut-off of 3,000 Daltons to obtain a final 10 mg/mL concentration. The crude eluted fraction contained the recombinant fusion protein of HIV-1 Tat, as expected.

A fusion protein consisting of Tat genetically fused to a fragment coding for a histidine-rich peptide, which permits binding to Ni-bound resins for a purification step, was thus obtained. The eluted fraction is then submitted to the carboxymethylation reaction.

Example 1

Tat Toxoid Preparation

Stage A: Carboxymethylation

The Tat protein/Histidine-rich peptide fusion protein, prepared as described above, was taken in or adjusted to: 8 M urea, 0.3 M Tris HCI, 10 mM Dithiotreitol, pH 8.4.

Iodoacetic acid (2.6 g) was added to 100 mL of the above-mentioned solution under inert atmosphere. The solution was incubated at 37° C in the dark and under inert atmosphere for 90 min. The reaction was blocked by adding 1 mL 98% β-mercaptoethanol, and the solution was incubated for 80 minutes under the same conditions as described above.

The solution derived from the preceding step was concentrated by means of an Amicon concentrator (Cat #8400) on a YM3 membrane (3,000 D threshold pore) until the concentration was 10 mg/mL.

Desalting was performed in a Cellufine GH25 column (MATREX) equilibrated with 300 mL of 4 M urea and 0.1 M HCl.

Stage B: Purifications

The eluted fraction was then ultrafiltered and treated with cyanogen bromide to cleave at the methionine position the amino terminus from the carboxymethylated product. Cyanogen bromide was added in excess under inert atmosphere in the ratio of about 50 moles CNBr per mole of methionine. This solution was stored/preserved in a closed flask for 24 h at 37° C. The excess of CNBr was evaporated under reduced pressure.

The solution thus obtained was then concentrated, diafiltered against a acetic acid/sodium acetate 0.05 M buffer solution of pH 5 by using a diafilter Amicon with a YM3 (3000 D threshold pore) membrane. The amount of inactive product obtained in solution was about 450 mg.

The solution was filtered through an ionic exchange SP-Sepharose FF column previously equilibrated with 200 mL of buffer A, and the product was eluted with a NaCl gradient.

The eluted fraction was again concentrated by diafiltration in the same Amicon system, and the obtained fraction was purified by gel filtration in a Sephacryl S (Pharmacia) column equilibrated with a phosphate buffer with pH 7.4. The final product was filtered through a 0.22 μm membrane and stocked at 4° C until use.

This product was submitted to the analysis described below and the pharmacological tests.

Analysis

Total amount of inactivated product as determined by the Bradford tests: 150 mg.

Polyacrylamide gel electrophoresis containing sodium dodecyl sulphate (SDS-PAGE), silver staining. (Phast System, Pharmacia, homogeneous gel 20% acrylamide): unique band of an expected molecular weight; no other bands were detected of lower or higher molecular weight values.

Electrophoresis by isoelectric gradient (Phast System, Pharmacia, GEL IEF 3-0): a single visible band was observed.

Western blot (Phast System, Pharmacia), monoclonal antibody from hybridoma 5G11: a single band was observed and there was no aggregated or degraded material observed.

Biological activity (induction of CAT gene in the cell line HeLa HIV-1-LTR CAT): no detectable activity observed.

Sequencing of the N-terminal region by the standard Edman's technique with an Applied Biosystems (model 477A) sequencer: the first 20 amino acids obtained were coincident to the expected sequence:

Glu - Pro - Val - Asp - Pro - Arg - Leu - Glu - Pro - Trp - Lys - His - Pro - Gly - Ser - Gln - Pro - Lys - Thr - Ala (SEQ ID NO:1)

Endotoxins (LAL test according to USP XXIII protocol): less than 0.5 endotoxic units per mg of protein were observed.

Sterility (according to USP XXIII protocol): fulfilled specifications.

Measurement of substitution grade: Ellman reagent used to determine the free sulphydryl groups by comparison with a standard curve dosing cysteines; by comparing the native Tat to carboxymethylated Tat, only 0.03% cysteines remained active within carboxymethylated Tat, resulting in 1 active cysteine per 3330 inactive cysteines.

A simple calculation shows that, in order to get a single Tat molecule with 7 active cysteines under these conditions, it would be necessary to have several kilograms of Tat protein. The inactivation was almost complete.

Example 2

Preparation of Nef Toxoid

For the preparation of the Nef toxoid by cloning, Nef sequence-derived oligonucleotides were used as primers to obtain the Nef cDNA by RT-PCR methods from HIV-1 infected cells. The same plasmid as used in Example 1 which contains the histidine-rich gene segment, which permits linkage to the Ni-column, was used. The production protocol and the purification are thus the same as described in Example 1, except that the cut was done by enterokinase digestion instead of CNBr. The obtained results were similar to those obtained with the Tat protein.

Example 3

IFNα- Toxoid Preparation

In this case, the plasmid does not code for a fusion protein. The interferon alpha protein was directly produced by recombinant DNA methodology without the use of a gene fragment which codes for a histidine-rich peptide. Alpha interferon was purified by column affinity chromatography with attached anti-interferon alpha monoclonal antibodies.

After elution, the protein was immediately inactivated according to the same protocol described for Example 1.

The results from analyses were identical to those obtained with Tat protein. Using a biological test showing a null antiviral activity (VSV on MDBK cells), it was concluded the biological inactivation was complete.

Example 4

Pharmacological Study: The Absence of Immunosuppressive Effect of Tat

A simple test exists to show the immunosuppressive effect of native Tat protein. Peripheral blood cells (PBMC) were incubated in a medium without serum with native or toxoid Tat protein at concentrations of 0 to 10 mg/mL. After 2 h, serum was added to a 10% final concentration, and cells were stimulated with the Staphylococcus enterotoxin B (SEB) or by a memory antigen "Protein Purified Derived" (PPD). After three days for SEB or 5 days for PPD, proliferation was evaluated.

A decrease in proliferation was observed in a dose-dependent manner for native Tat, but a decrease was not observed for the toxoid.

In FIG. 1, the left side bars correspond to native Tat and the right side bars correspond to the compound of Example 1 (Tat toxoid). In the abscissa, the product concentrations are expressed in μg/mL as 0, 1, 3, and 10. In the ordinate, the percentage of T cell proliferation is indicated. The control corresponds to a 0 μg/mL Tat concentration. The results indicate that native Tat inhibited cellular proliferation, whereas the compound of Example 1 was not effective.

Example 5

Immunungenicity of Tat Toxoid in Mice, Production of Neutralizing Antibodies

Tat toxoid was prepared as in Example 1 for mice immunization. The immunization protocol is the one classically used:

A (1:1) emulsion of the toxoid which contains 20 μg of product with a complete Freund adjuvant (100 μL) was injected into mice by the intramuscular route, at day 0.

Memory antigen in incomplete Freund adjuvant (5 μg) was injected at days 21 and 35. Mice serum was extracted at days −2, 28 and 40, and anti-Tat antibodies were evaluated by ELISA on plates sensitized with native (chemically untreated) Tat protein or the compound of Example 1. Sera were tested at 1:1000 dilutions. The results obtained are expressed in optical density (OD) units for 3 immunized mice (1 to 3) and 3 non-immunized mice (4 to 6), as shown in the following table:

| | | Native Tat | Toxoid Tat |
|---|---|---|---|
| Mouse 1 | day −2 | 0.3 | 0.3 |
| | day 28 | 1.6 | 1.5 |
| | day 40 | 2 | 2.1 |
| Mouse 2 | day −2 | 0.2 | 0.3 |
| | day 28 | 1.9 | 1.8 |
| | day 40 | 2.2 | 2.2 |
| Mouse 3 | day −2 | 0.4 | 0.4 |
| | day 28 | 1.7 | 1.5 |
| | day 40 | 1.9 | 2.2 |
| Mouse 4 | day −2 | 0.2 | 0.2 |
| | day 28 | 0.3 | 0.2 |
| | day 40 | 0.3 | 0.3 |
| Mouse 5 | day −2 | 0.4 | 0.4 |
| | day 28 | 0.4 | 0.3 |
| | day 40 | 0.3 | 0.3 |
| Mouse 6 | day −2 | 0.3 | 0.3 |
| | day 28 | 0.4 | 0.3 |
| | day 40 | 0.3 | 0.3 |

These results indicate that toxoid immunized mice produced antibodies which recognized the native protein and the toxoid in a similar manner.

These antibodies were also neutralizing. This fact was established by 2 different tests:

The Tat protein inactivation test: A culture of a HeLa-HIV1-LTR-CAT cell line stably transfected with the plasmid containing the HIV-1 long terminal repeat (LTR), which codes for Chloramphenicol Acetyl Transferase (CAT) under the control of the LTR promoter, was supplied with native or toxoid Tat protein pre-incubated for 1 h with serum (1:50 dilution) from immunized or non-immunized mice (day 0 or day 40). The native Tat protein (5 μg/mL) entered the cells and exerted its transactivation effect on the LTR from HIV-1 to induce CAT protein expression.

After 48 h, cells were lysed, and the CAT protein amount was determined by an ELISA (Boehringer) test. Results are expressed in OD units:

| | Mouse number per day | OD units (CAT) |
|---|---|---|
| Native tat | | 1.4 |
| Toxoid Tat | | 0.2 |
| Native Tat + mouse serum | 2/D 0 | 1.5 |
| Native Tat + mouse serum | 6/D 0 | 1.3 |

-continued

|  | Mouse number per day | OD units (CAT) |
|---|---|---|
| Native Tat + mouse serum | 2/D 40 | 0.3 |
| Native Tat + mouse serum | 6/D 40 | 1.4 |

These results indicate that immunized mice serum (mouse 20; 2) contained neutralizing antibodies for the native protein. This was not the case for the non-immunized mice sera.

Moreover, when the antibodies produced by the toxoid immunized mice in the above-described immunosuppression test were used for the pharmacology study (1:50 dilution), the immunosuppressive effect of native Tat protein was blocked.

All of these results indicate that the compound of Example 1 is immunogenic and induces an immune response which neutralizes the native protein.

Example 6

Immunogenicity of IFNα Toxoid in Mice, Neutralizing Antibodies Production

The IFNα toxoid as prepared in Example 3 was used for mice immunization. The immunization protocol was the one classically used: mice were intramuscularly injected with a 100 μL emulsion (1:1) with complete Freund adjuvant containing 20 μg of product at day 0 and with memory antigen in incomplete Freund adjuvant (5 μg) at days 21, 35 and 45. Mice serum was extracted at days 2,28 and 50 and analyzed by ELISA on sensitized plates either with chemically untreated native IFNα or with the toxoid.

Sera was tested at 1:1000 dilution. Results expressed in OD units for 3 immunized (1 to 3) and 3 not immunized (4 to 6) mice are shown in the following table:

|  |  | Native IFNα | Toxoid IFNα |
|---|---|---|---|
| Mouse 1 | day −2 | 0.3 | 0.3 |
|  | day 28 | 1 | 0.9 |
|  | day 50 | 2.1 | 2.1 |
| Mouse 2 | day −2 | 0.2 | 0.3 |
|  | day 28 | 1.2 | 1.1 |
|  | day 50 | 1.9 | 2 |
| Mouse 3 | day −2 | 0.4 | 0.4 |
|  | day 28 | 0.8 | 0.9 |
|  | day 50 | 2 | 2.1 |
| Mouse 4 | day −2 | 0.1 | 0.1 |
|  | day 28 | 0.2 | 0.2 |
|  | day 50 | 0.1 | 0.1 |
| Mouse 5 | day −2 | 0.2 | 0.2 |
|  | day 28 | 0.2 | 0.2 |
|  | day 50 | 0.2 | 0.3 |
| Mouse 6 | day −2 | 0.3 | 0.3 |
|  | day 28 | 0.2 | 0.3 |
|  | day 50 | 0.3 | 0.3 |

These results indicate that toxoid-immunized mice produced antibodies recognizing the native protein and the toxoid in a similar manner. In addition, these results confirm the innocuity of toxoid immunization, since the mice tolerated immunization well.

These antibodies are also neutralizing. This fact was established by the classic VSV test on MDBK cells. Normally, cells become VSV-lysis resistant by the addition of 1–10 units of IFNα. When incubation was performed with native IFNα with the serum of mouse 1 or 4 (D0–D50) at a 1:50 dilution, lysis was observed only in the case of native INFα which was preincubated with the serum of mouse 1 at D 50.

This example indicates that the compound of Example 3 is immunogenic and induces the production of antibodies which neutralize the native protein.

Example 7

Toxoid Nef Immunogenicity in Mice

The toxoid Nef, as prepared in Example 2, was used for mice immunization. The classic protocol was used: 100 μL of an (1:1) emulsion of Nef toxoid containing 20 μg of product in complete Freund adjuvant was infected intramuscularly into mice at days 21 and 35. Mice serum was extracted at days −2,28 and 40 and analyzed by ELISA with sensitized plates either with chemically untreated native recombinant Nef or the Nef toxoid of Example 2. Sera was tested at a 1:1000 dilution. The results which were obtained, expressed as OD units for the 3 immunized (1 to 3) and the 3 non-immunized (4 to 6) mice, are shown in the following table:

|  |  | Native Nef | Toxoid Nef |
|---|---|---|---|
| Mouse 1 | day −2 | 0.1 | 0.1 |
|  | day 28 | 1 | 0.9 |
|  | day 50 | 2.1 | 2.1 |
| Mouse 2 | day −2 | 0.1 | 0.1 |
|  | day 28 | 1.5 | 1.4 |
|  | day 50 | 1.9 | 2 |
| Mouse 3 | day −2 | 0.1 | 0.1 |
|  | day 28 | 0.8 | 0.9 |
|  | day 50 | 1.8 | 1.6 |
| Mouse 4 | day −2 | 0.1 | 0.1 |
|  | day 28 | 0.1 | 0.1 |
|  | day 50 | 0.1 | 0.1 |
| Mouse 5 | day −2 | 0.1 | 0.1 |
|  | day 28 | 0.1 | 0.1 |
|  | day 50 | 0.1 | 0.1 |
| Mouse 6 | day −2 | 0.1 | 0.1 |
|  | day 28 | 0.1 | 0.1 |
|  | day 50 | 0.1 | 0.1 |

These results indicate that mice immunizedwith the Nef toxoid of Example 2 produced antibodies which recognized the native protein and the toxoid in a similar manner. In addition, the results confirmed the toxoid-Nef immunization innocuity because the mice have well-tolerated the immunization.

Example 8

Effect of Tat and IFNα Toxoid Immunized Mice on the In Vitro Infection by HIV-1

A test of in-vitro induced immunosuppression was also developed. This test was performed in the following manner:

Peripheral blood cells (PBMCs) from a healthy subject were infected by an HIV-1 lymphotrophic (HIV-HTLVIIIB) strain. After phytohemaglutinin (PHA) stimulation and 6 days of culture in the presence of lnterleukin-2 (IL-2), cells were irradiated. Irradiated cells are suppressive, capable of inhibiting PBMC proliferation by stimulating antigens like SEB or PPD. This immunosuppressive effect was not linked to the residual virus after irradiation because reverse transcriptase or p24 antigen assays were negative in the supernatant fluids.

When a control cell preparation without viruses was irradiated in the same manner 6 days after stimulation with PHA, and then added to cells stimulated by SEB or PPD, no inhibition of proliferation was observed whatsoever. The inhibitory effect was due to the HIV-1 virus. J. F. Zagury et al. (attorney handwritten notes) critical role of the Tat and IFNα in the HIV-1 induced immunosuppression leading to AIDS, *Cell Pharmcol. AIDS Sciences* 3:97–103 (1996)) describe that this suppressive cell genesis is dependent on both IFNα and the Tat protein because neutralizing antibodies against these proteins inhibit suppressive cell formation.

In a similar experiment when sera (1:50 dilutions) of Tat and IFNα toxoid (Examples 1 and 3) immunized mice was added, they blocked suppressive cells generation. This was not the case with non-immunized (negative controls) or pre-immunized mice sera. When only Tat toxoid immunized mice serum was used, the immunosuppression was not blocked. On the contrary, the IFNα toxoid immunized mice serum produces 70% inhibition of immnunosuppression.

When both anti-Tat and anti-IFNα sera were combined, suppressive cell generation was completely blocked. These results were obtained by utilizing different virus batches, mainly primary isolates. This indicates that antibodies to Tat obtained with one toxoid can also show a cross-reactivity. These results, described by J. F. Zagury et al. (op. cit)(1996), confirm the inhibitory effect of the combined Tat and IFNα immunized sera on the immunosuppressive state in AIDS patients. They also confirm the initiator role of Tat and the determinant role of IFNα in this immunosuppression (See D. Zagury et aL, IFN and Tat involvement in the immunosuppression of uninfected T cells and C-C-chemokine decline in AIDS *Proc. Natl. Acad. Sci. USA,* 1998, in press).

The results of these studies indicate the necessity of inhibiting the effects of extracellular Tat by inducing a neutralizing antibody response, by acting, if possible, on Tat production through the induction of a cellular immune response.

Example 9

Immunogenicity and Innocuity of Tat and IFNα Toxoids Either Combined or Not, in Humans; Compatibility with Chemotherapies Tables 1, 2 and 3 describe the results obtained during a phase 1 trial using the toxoids of Examples 1 and 3 in 50:50 emulsions with ISA 51 (SEPPIC): volume of 1 mL containing 100 μg of active agent according to the invention. The responses to the IFNα toxoid (data not shown) were similar to those already described in papers from Gringeri el al. in *J. AIDS* 7:978–988 (1994) and 13: 55–67 (1996) on a toxoid prepared by formolization.

Table 1: Descriptions of patients included in phase 1 trial.
Table 2: Biological parameters at initial and final times (generally 6 months).
Table 3: Analysis of the anti-Tat specific response.

TABLE 1

Age at the time of seroconversion and anti-retroviral treatment. Demography of patients immunized against HIV-1 Tat.

| Code | Age | Sex | Risk factor | Age at the time of seroconversion | Antiviral treatment | Antiviral treatment with proteinase | Anti-IFNα immunization |
|---|---|---|---|---|---|---|---|
| 1 | 25 | M | Hemophiliac | 12 | Y | Y | Y |
| 2 | 39 | M | Hemophiliac | 26 | N | N | N |
| 3 | 33 | F | Sexual partner | 26 | Y | Y | Y |
| 4 | 38 | M | Hemophiliac | 23 | N | N | Y |
| 5 | 25 | M | Hemophiliac | 12 | N | N | N |
| 6 | 31 | M | Hemophiliac | 19 | Y | N | N |
| 7 | 19 | M | Hemophiliac | 7 | N | N | Y |
| 8 | 35 | M | Hemophiliac | 22 | Y | N | Y |

TABLE 1-continued

Age at the time of seroconversion and anti-retroviral treatment. Demography of patients immunized against HIV-1 Tat.

| Code | Age | Sex | Risk factor | Age at the time of seroconversion | Antiviral treatment | Antiviral treatment with proteinase | Anti-IFNα immunization |
|---|---|---|---|---|---|---|---|
| 9 | 26 | M | Hemophiliac | 15 | N | N | N |
| 10 | 38 | M | Hemophiliac | 26 | N | N | N |
| 11 | 26 | M | Hemophiliac | 14 | Y | Y | N |
| 12 | 33 | M | Hemophiliac | 20 | Y | Y | N |
| 13 | 40 | F | Sexual partner | 36 | N | N | N |
| 14 | 26 | F | Sexual partner | 20 | N | N | Y |

TABLE 2

D4 cells count in absolute values, HIV-1 plasma viremia and antigenemia in 14 seropositive patients immunized with examples 1 or 3 products.

| Code | Follow-up in months | CD4 cell count in cell/mm$^3$ Before | CD4 cell count in cell/mm$^3$ After | HIV-1 viremia Before | HIV-1 viremia After | anti-HIV antigens Before | anti-HIV antigens After |
|---|---|---|---|---|---|---|---|
| 1 | 8 | 284(28.4%) | 345(34.5%) | 5.75 | 5.71 | 11 | 4 |
| 2 | 8 | 453(16.8%) | 534(18.4%) | 2.06 | 2.15 | 32 | 3 |
| 3 | 12 | 227(28.4%) | 345(34.5%) | 0.35 | <0.005 | 17 | 4 |
| 4 | 3 | 287(22.1%) | 262(21.0%) | 0.49 | 0.70 | 3 | 3 |
| 5 | 5 | 282(28.2%) | 319(22.8%) | 3.34 | 0.91 | 4 | 4 |
| 6 | 9 | 224(11.8%) | 294(12.8%) | 5.23 | 3.90 | 3 | 3 |
| 7 | 3 | 313(24.1%) | 443(23.3%) | 5.39 | 5.55 | 4 | 4 |
| 8 | 4 | 275(30.6%) | 314(31.4%) | 4.12 | 3.18 | 5 | 4 |
| 9 | 6 | 274(8.3%) | 386(9.9%) | 5.08 | 5.74 | 4 | 5 |
| 10 | 8 | 295(22.7%) | 372(26.6%) | 4.02 | 3.9 | 5 | 4 |
| 11 | 4 | 219(16.9%) | 235(23.5%) | 4.01 | <1 | 8 | 3 |
| 12 | 12 | 272(20.9%) | 340(30.9%) | 4.74 | 2.30 | n.a. | 4 |
| 13 | 9 | 435(33.5%) | 478(28.1%) | 4.30 | 4.07 | 3 | 4 |
| 14 | 3 | 257(13.5%) | 274(13.7%) | 2.05 | 2.90 | 3 | 3 |

TABLE 3

Immunogenicity of anti-HIV-1 Tat immunization in HIV-1 seropositive patients.

| Patient code | Immunization type A/B | Anti-tat antibodies response | Anti-tat antibodies in OD units Basal | Anti-tat antibodies in OD units Pic | Responses DH | Responses CMI |
|---|---|---|---|---|---|---|
| 1 | B | Y | 0.240 | 1.230 | n.a. | n.a. |
| 2 | A | Y | 0.104 | 1.526 | n.a. | POS |
| 3 | B | Y | 0.217 | 0.537 | NEG | NEG |
| 4 | B | Y | 0.214 | 1.063 | POS | n.a. |
| 5 | A | Y | 0.446 | 1.612 | n.a. | n.a. |
| 6 | A | Y | 0.213 | 0.664 | NEG | NEG |
| 7 | A | Y | 0.204 | 1.139 | n.a. | n.a. |
| 8 | B | Y | 0.104 | 1.045 | POS | POS |
| 9 | A | Y | 0.422 | 0.812 | NEG | n.a. |
| 10 | B | Y | 0.125 | 1.492 | n.a. | n.a. |
| 11 | A | Y | 0.252 | 0.682 | NEG | n.a. |
| 12 | A | Y | 0.410 | 2.219 | POS | POS |
| 13 | A | Y | 0.162 | 0.508 | POS | POS |
| 14 | B | Y | 0.120 | 2.012 | n.a. | n.a. |

DH : Delayed hypersensitivity
CMI: Cell mediated immunity

What is claimed is:

1. A substantially purified retroviral regulatory protein or fragment thereof, wherein said protein or fragment thereof is carboxymethylated, and wherein said protein or fragment thereof is, or is derived from, the Tat protein of HIV-1.

2. A substantially purified carboxymethylated Tat protein or fragment thereof from HIV-1 having the following characteristics:

(a) single band on SDS-PAGE; and
(b) single band on isoelectric gradient electrophoresis.

3. A pharmaceutical composition comprising at least one protein or fragment thereof of claim 1 or claim 2, together with a pharmaceutically acceptable carrier.

4. The composition of claim 3 further comprising:

(a) an ajuvant;
(b) an anti-retroviral immunogen; or
(c) mixtures thereof.

5. The composition of claim 4, wherein said anti-retroviral immunogen (b) comprises envelope protein GP 160 from HIV-1 or fragment thereof, transmembrane protein GP 41 from HIV-1 or fragment thereof, viral capsid gag protein or pol protein.

6. The composition of claim 4, wherein said anti-reroviral immunogen (b) comprises Nef protein, Rev protein, Vpr protein, Tax protein, Vif protein or fragments thereof.

7. The composition of claim 4, wherein said anti-retroviral immunogen (b) is carboxymethylated.

8. The composition of claim 3, further comprising carboxymethylated interferon alpha protein or fragment thereof.

9. A fusion protein comprising a retroviral regulatory protein or fragment thereof fused to a heterologous polypeptide, wherein said retroviral regulatory protein or fragment thereof is carboxymethylated, and wherein said protein or fragment thereof is, or is derived from, the Tat protein of HIV-1.

10. The fusion protein of claim 9, wherein said heterologous polypeptide contains at least one histidine.

* * * * *

SEQUENCE LISTING

<160> NUMBER OF SEQ ID NOS: 1

<210> SEQ ID NO 1
<211> LENGTH: 20
<212> TYPE: PRT
<213> ORGANISM: Human Immunodeficiency Virus Tat protein

<400> SEQUENCE: 1

Glu Pro Val Asp Pro Arg Leu Glu Pro Trp Lys His Pro Gly Ser Gln
 1               5                  10                  15

Pro Lys Thr Ala
         20